(12) United States Patent
Ford et al.

(10) Patent No.: US 11,923,044 B1
(45) Date of Patent: Mar. 5, 2024

(54) SYSTEMS, METHODS, AND APPARATUSES TO PREDICT PROTEIN SEQUENCE AND STRUCTURE

(71) Applicant: Amazon Technologies, Inc., Seattle, WA (US)

(72) Inventors: Alexander Sewall Ford, Seattle, WA (US); Vanessa Nguyen, Seattle, WA (US); Layne Christopher Price, Seattle, WA (US); Franziska Seeger, Seattle, WA (US); Yen Ling Adelene Sim, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 762 days.

(21) Appl. No.: 16/896,907

(22) Filed: Jun. 9, 2020

(51) Int. Cl.
*G16B 15/00* (2019.01)
*G16B 30/20* (2019.01)
*G16B 40/00* (2019.01)

(52) U.S. Cl.
CPC ............. *G16B 15/00* (2019.02); *G16B 30/20* (2019.02); *G16B 40/00* (2019.02)

(58) Field of Classification Search
CPC ......... G16B 15/00; G16B 30/20; G16B 40/00
See application file for complete search history.

(56) References Cited

PUBLICATIONS

Ho. Nature Methods 17: 79-85. 2020. (Year: 2020).*
AlQuraishi. Cell Systems 8: 292-301. 2019. (Year: 2019).*
Sucholutsky. PeerJ Computer Science 5: e210. 2019. (Year: 2019).*
Mrozek. Journal of Grid Computing 13: 561-585. 2015. (Year: 2015).*
Alquraishi, Mohammed, End-to-End Differentiable Learning of Protein Structure, Cell Systems, Apr. 24, 2019, pp. 292-301 (14 pages), vol. 8.
Anand, Namrata and HUANG, Po-Ssu, Generative Modeling for Protein Structures, 32nd Conference on Neural Information Processing Systems (NeurIPS 2018), Montreal, Canada, 12 pgs.
Anand, Namrata et al., Fully Differentiable Full-Atom Protein Back-Bone Generation, Published as a workshop paper at International Conference on Learning Representations (ICLR) (2019), 10 pgs.
Arnold, Frances H., Design by Directed Evolution, Acc. Chem. Res. (1998), pp. 125-131, vol. 31/ No. 31.
Bileschi, Maxwell L. et al., Using Deep Learning to Annotate the Protein Universe, bioRxiv preprint; 2019, 21 pgs., https://doi.org/10.1101/626507.
Brandenberg, Oliver F. et al., Exploiting and Engineering Hemoproteins for Abiological Carbene and Nitrene Transfer Reactions, Curr Opin Biotechnol.; Oct. 2017, pp. 102-111, vol. 47.
Butler, Keith T. et al., Machine learning for molecular and materials science, Nature; Jul. 2018, pp. 547-555, vol. 559, https://doi.org/10.1038/s41586-018-0337-2.
Chen, Hongming et al., The rise of deep learning in drug discovery, Drug Discovery Today; Jun. 2018, pp. 1241-1250, vol. 23 / No. 6.
Cornish-Bowden, Athel, Current IUBMB recommendations on enzyme nomenclature and kinetics, Perspectives in Science; 2014, pp. 74-87.
Costello, Zak; Martin Garcia, Hector, How To Hallucinate Functional Proteins—A Preprint, arXiv: 1903.00458v1 preprint; 2019, 13 pgs., https://arxiv.org/pdf/1903.00458.pdf.
Dalkiran, Alperen et al., ECPred: a tool for the prediction of the enzymatic functions of protein sequences based on the EC nomenclature, BMC Bioinformatics (2018) 19:334, 13 pgs.
Devlin, Jacob et al., BERT: Pre-training of Deep Bidirectional Transformers for Language Understanding, arXiv: 1810.04805; 2019, 16 pgs., https://arxiv.org/pdf/1810.04805.pdf.
Dou, Jiayi et al., Sampling and energy evaluation challenges in ligand binding protein design, Protein Science; 2017, pp. 2426-2437, vol. 26, https://onlinelibrary.wiley.com/doi/epdf/10.1002/pro.3317.
Fowler, Douglas M.; Fields, Stanley, Deep mutational scanning: a new style of protein science, Nat Methods. Aug. 2014; 11(8), 17 pgs.
Fox, Naomi K. et al., SCOPe: Structural Classification of Proteins—extended, integrating SCOP and ASTRAL data and classification of new structures, Nucleic Acids Research (2013), pp. D304-D309, vol. 42, Database issue.
Hadadi, Noushin et al., Enzyme annotation for orphan and novel reactions using knowledge of substrate reactive sites, Proceedings of the National Academy of Science (PNAS); 2019, 10 pgs., https://www.pnas.org.
Hopf, Thomas A. et al., Mutation effects predicted from sequence co-variation, Nat. Biotechnol. (2017), 26 pgs.
Huang, Po-Ssu et al., The coming of age of de novo protein design, Nature, 537; Sep. 15, 2016, pp. 320-327, https://www.bakerlab.org/wp-content/uploads/2016/09/HuangBoyken_DeNovoDesign_Nature2016.pdf.

(Continued)

*Primary Examiner* — Soren Harward
*Assistant Examiner* — Robert James Kallal
(74) *Attorney, Agent, or Firm* — Nicholson De Vos Webster & Elliott LLP

(57) ABSTRACT

Techniques for predicting a protein sequence are described. An exemplary method includes receiving a request to predict a missing area of a protein's primary sequence and a corresponding three-dimensional position of the missing area; applying a machine learning model to backbone Cartesian coordinates of the protein's primary sequence and a protein vector of a representation of the protein's primary sequence including the missing area to predict a missing area of the protein primary sequence and a corresponding three-dimensional position for the missing area, wherein the machine learning model is selected from the group consisting of: an attention-based machine learning model, a bidirectional long short term memory-based model, and a convolutional neural network-based model; and outputting a result of the machine learning model.

20 Claims, 12 Drawing Sheets

(56) References Cited

PUBLICATIONS

Jeske, Lisa et al., Brenda in 2019: a European ELIXIR core data resource, Nucleic Acids Research; 2018, 8 pgs., vol. 47, https://pdfs.semanticscholar.org/c1f4/0918851e899fbdc0cdffea9f162acab67210.pdf?_ga=2.169725993.94394913.1658075614-1645612148.1658075614.

Karami, Yasaman et al., DaReUS-Loop: accurate loop modeling using fragments from remote or unrelated proteins, Scientific Reports (2018), 12 pgs.

Li, Yu et al., DEEPre: sequence-based enzyme EC number prediction by deep learning, Bioinformatics; 2017, pp. 760-769, vol. 34.

LIU; Yinhan et al., ROBERTa: A Robustly Optimized BERT Pretraining Approach, arXiv preprint arXiv:1907.11692; 2019, 13 pgs.

Lopes, Pedro E.M et al., Current Status of Protein Force Fields for Molecular Dynamics Simulations, Molecular modeling of proteins, Ch 3. (2015), pp. 47-71.

Mizuguchi, Kenji et al., HOMSTRAD: A database of protein structure alignments for homologous families, Protein Science (1998), pp. 2469-2471.

Nguyen, Thin et al., GraphDTA: prediction of drug-target binding affinity using graph convolutional networks, bioRxiv preprint (2019), 16 pgs., https://doi.org/10.1101/684662.

Ozturk, Hakime et al., DeepDTA: Deep Drug-Target Binding Affinity Prediction, arXiv: 1801.10193; 2018, 18 pgs.

Park, Hahnbeom et al., Protein Loop Modeling Using a New Hybrid Energy Function and Its Application to Modeling in Inaccurate Structural Environments, PLoS One, Nov. 24, 2014, 18 pgs.

Petrovic, Dusan et al., Conformational dynamics and enzyme evolution, J. R. Soc. Interface 15; 2018, 18 pgs., http://dx.doi.org/10.1098/rsif.2018.0330.

Rao, Roshan et al., Evaluating Protein Transfer Learning with TAPE, 33rd Conference on Neural Information Processing Systems (NeurIPS), Vancouver, Canada; 2019, 13 pgs., https://papers.nips.cc/paper/2019/file/37f65c068b7723cd7809ee2d31d7861c-Paper.pdf.

Riesselman, Adam et al., Accelerating Protein Design Using Autoregressive Generative Models, bioRxiv preprint; 2019, 7 pgs., https://www.biorxiv.org/content/10.1101/757252v1.full.pdf.

Riesselman, Adam J.; Ingraham, John B.; Marks, Debora S., Deep generative models of genetic variation capture mutation effects, Nat Methods; 2018, 25 pgs., https://arxiv.org/ftp/arxiv/papers/1712/1712.06527.pdf.

Rives, Alexander et al., Biological Structure and Function Emerge From Scaling Unsupervised Learning to 250 Million Protein Sequences, bioRxiv preprint; 2019, 25 pgs., https://doi.org/10.1101/622803.

Romero, Philip A.; Arnold, Frances H., Exploring protein fitness landscapes by directed evolution, Nat Rev Mol Cell Biol, 10; Dec. 2009, 25 pgs., https://authors.library.caltech.edu/16942/3/nihms251972.pdf.

Ryu, Jae Yong et al., Deep learning enables high-quality and high-throughput prediction of enzyme commission numbers, Proceedings of the National Academy of Sciences (PNAS); Jul. 9, 2019, pp. 13996-14001, vol. 116/ No. 28.

Strodthoff, Nils et al., UDSMProt: Universal Deep Sequence Models for Protein Classification, bioRxiv preprint; 2019, 11 pgs., https://doi.org/10.1101/704874.

Tian, Siyang et al., CypReact: A Software Tool for in silico Reactant Prediction for Human Cytochrome P450 Enzymes, J. Chem. Inf. Model. 58; 2018, pp. 1282-1291.

Vaswani, Ashish et al., Attention Is All You Need, 31st Conference on Neural Information Processing Systems (NIPS), Long Beach, CA;; 2017, 15 pgs.

Wrenbeck, Emily E. et al., Single-mutation fitness landscapes for an enzyme on multiple substrates reveal specificity is globally encoded, Nature Communications, 8:15695; 2017, 10 pgs.

Wu, Zachary et al., Machine learning-assisted directed protein evolution with combinatorial libraries, Proceedings of the National Academy of Sciences (PNAS); Apr. 30, 2019, pp. 8852-8858, vol. 116 /No. 18.

Yang, Kevin K et al., Machine learning-guided directed evolution for protein engineering, arXiv:1811.10775; Apr. 19, 2019, 15 pgs.

Yu, Jiahui et al., Generative Image Inpainting with Contextual Attention, Proceedings of the IEEE Conference on Computer Vision and Pattern Recognition (2018), 15 pgs., https://arxiv.org/pdf/1801.07892.pdf.

Zanger, Ulrich M.; Schwab, Matthias, Cytochrome P450 enzymes in drug metabolism: Regulation of gene expression, enzyme activities, and impact of genetic variation, Pharmacology & Therapeutics (2013), pp. 103-141, vol. 138.

Chen, Lifan, et al. "TransformerCPI: improving compound-protein interaction prediction by sequence-based deep learning with self-attention mechanism and label reversal experiments." Bioinformatics 36.16 (2020): 4406-4414.

Karimi, Mostafa, et al. "DeepAffinity: interpretable deep learning of compound-protein affinity through unified recurrent and convolutional neural networks." SUPPLEMENTAL Bioinformatics 35.18 (2019): 3329-3338.

Li, Shuya, et al. "MONN: a multi-objective neural network for predicting compound-protein interactions and affinities." Cell Systems 10.4 (2020): 308-322.

Non-Final Office Action, U.S. Appl. No. 16/896,877, dated Jul. 27, 2023, 25 pages.

Serrano.Academy,"A friendly introduction to Recurrent Neural Networks," uploaded Aug. 18, 2017 Retrieved from Internet:<https://Awww.youtube.com/watch?v=UNmqTiOnRfg>.

Shankar, Shiv, and Sunita Sarawagi. "Posterior attention models for sequence to sequence learning." International Conference on Learning Representations. 2018.

Notice of Allowance, U.S. Appl. No. 16/896,877, dated Nov. 9, 2023, 7 pages.

* cited by examiner

SYSTEMS, METHODS, AND APPARATUSES TO PREDICT PROTEIN SEQUENCE AND STRUCTURE

BACKGROUND

Proteins are biological macromolecules composed of sequences of amino acids that carry out a host of functions in all living organisms Amino acids each have unique biochemical properties that interact with other amino acids in a protein sequence to dictate a protein's fold and functionality. The mechanisms that underlie protein folding have been studied by biochemists for decades yet remain ambiguous. However, it is clear that the protein folding mechanism is dictated by its amino acid sequence.

BRIEF DESCRIPTION OF DRAWINGS

Various embodiments in accordance with the present disclosure will be described with reference to the drawings, in which.

DETAILED DESCRIPTION

The present disclosure relates to methods, apparatus, systems, and non-transitory computer-readable storage media for predicting missing areas of a protein's primary sequence and its corresponding three-dimensional position.

Current deep learning applications to protein design primarily predict the structure of a given sequence. However, a deep learning model capable of protein design rather than just protein structure prediction must be able to learn a relationship between a given sequence and structure. The structure prediction task is similar to image inpainting, in which a model is tasked with generating a contextually reasonable completed image given an image with some ablated region.

In addition to requiring an input sequence to predict structure, these networks use alternative representations of protein structure such as a distance matrix or a sequence of torsional angles rather than an explicit Cartesian representation. This make interpreting the model's internal representation of the structure difficult to understand. The parameters of a network that intakes and outputs a Cartesian representation of protein structure can be more readily understood as the implicit factors from the sequence and structure that contribute to protein folding.

Detailed herein are embodiments for predicting a means missing areas of a protein's primary sequence and its corresponding three-dimensional position based off of a known residue and position of the remaining amino acids in the protein using one or more machine learning models. In some embodiments, multiple layers of a multi-headed self-attention model predict correlated areas of missing protein sequence and structure information. As such, the output of the model can be used to predict the three-dimensional structure of a protein.

Embodiments of the machine learning model are capable of reconstructing both a protein sequence and structure from an ablated protein. The machine learning model only needs the contextual sequence and atomic coordinates to generate an amino acid sequence and corresponding Cartesian coordinates to fill the ablated region, making it amenable to be used upstream of other computational modeling tasks.

Figure 1:
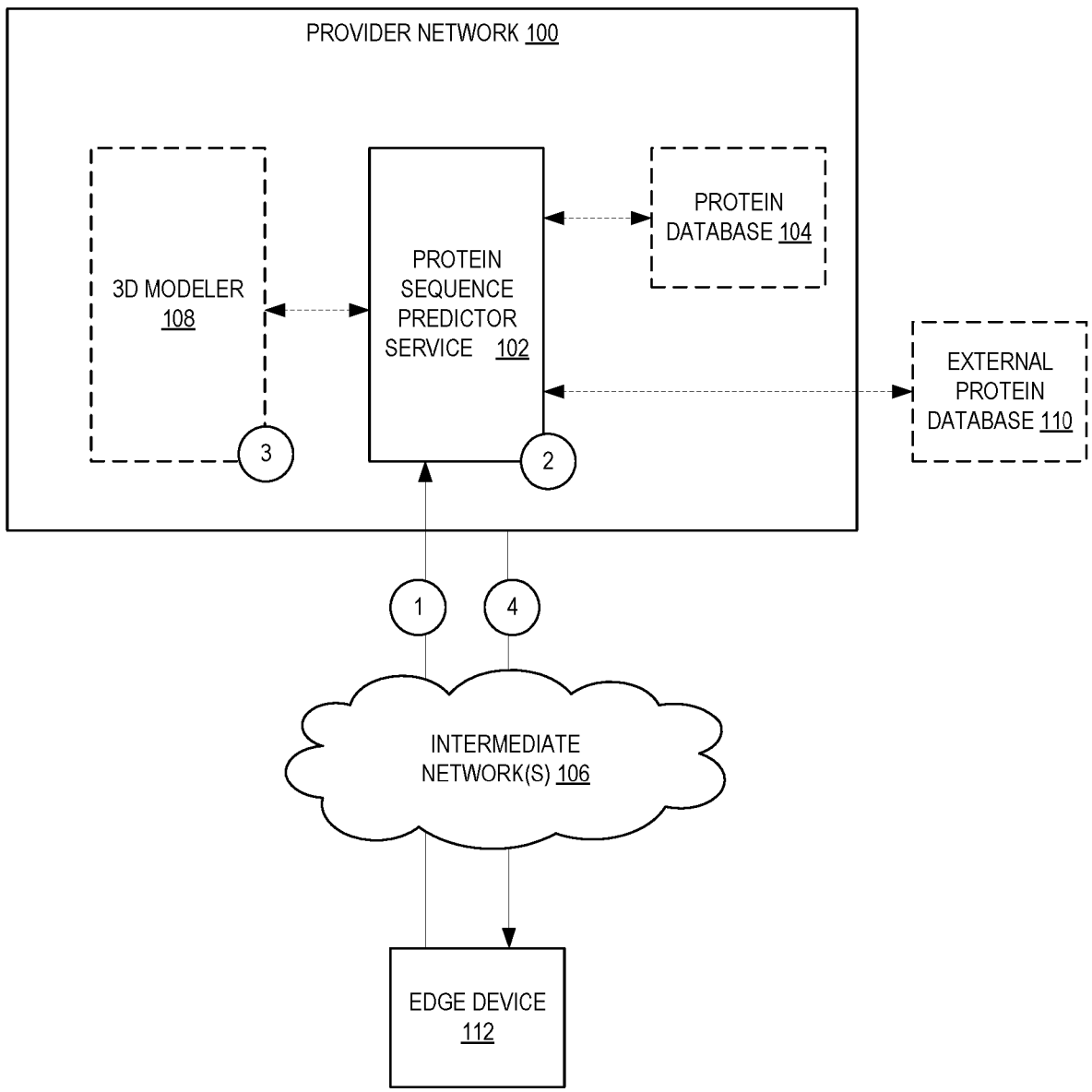
FIG. 1 illustrates embodiments of a system to predict missing areas of a protein's primary sequence and its corresponding three-dimensional position.

FIG. 1 illustrates embodiments of a system to predict missing areas of a protein's primary sequence and its corresponding three-dimensional position. As shown, a protein sequence predictor service 102 predicts using a machine learning model, according to a request, a protein sequence and coordinates of an ablated region. In some embodiments, the request includes a representation of protein primary sequence, backbone Cartesian coordinates for the primary sequence, and an indication of ablations (and/or, in some instances, regions of missing electron density) within the primary sequence. In some embodiments, the request includes conditioned versions of that information. In some embodiments, the output of the protein sequence predictor service 102 is a probability of each of the twenty amino acids as well as heavy atom backbone coordinates.

In some embodiments, the indication of regions of ablation may be a set of mask tokens in the protein primary sequence. Of course, other means of indicating a length of an ablated region may be used. Note that during training, the length of a location of an ablated region is varied with model iterations.

In some embodiments, an embedding of the machine learning model embeds the protein primary sequence into a high dimensional space. In some embodiments, the primary sequence is represented as 21 unique integers with a single integer representing noncanonical amino acids. The sequence is embedded into a higher dimensional space to allow for the expression of shared properties between the amino acids.

Additionally, in some embodiments, the Cartesian coordinates of the primary sequence are processed through a layer of convolutions to capture features distant in sequence space. For example, the coordinates to the center of mass of the protein may be centered and scaled by the radius of gyration of the structure to make the network more robust to structures of varying size. The embedded sequence and processed coordinates are combined (e.g., concatenated in some instances).

Following the combined embedded sequence and processed coordinates are one or more layers. In some embodiments, an attention-based (such as a transformer-based) architecture is used. In this architecture, the combined embedded sequence and processed coordinates are added to a sinusoidal positional encoding. Then self-attention is calculated on this combined representation of the proteins sequence and structure via a multi-layer attention encoder and the final attended sequence and structure is passed through a final convolutional layer to predict the sequence and coordinates of the ablated region. The final output is the probability of each of the twenty amino acids as well as heavy atom backbone coordinates.

In some embodiments, the protein sequence predictor service 102 is a convolution-based model. For example, the combined embedded sequence and processed coordinates are provided to a sequence of residual convolutional blocks to perform convolutions of a set channel dimension with a final position-independent, linear projection output from a fully connected network as a probability of each of the twenty amino acids as well as heavy atom backbone coordinates.

In some embodiments, the protein sequence predictor service 102 is a bidirectional long short term memory (BiLSTM)-based model. For example, the combined embedded sequence and processed coordinates are provided to a multi-layer BiLSTM network, each LSTM of which has a plurality (e.g., 150) dimensional hidden channels. A position-independent, linear projection using a fully connected layer provides the output which is the probability of each of the twenty amino acids as well as heavy atom backbone coordinates.

In some embodiments, the request includes already combined embedded sequence and processed coordinates which are then fed into a BiLSTM-based architecture, an attention-based encoder, or convolutional neural network (CNN)-based architecture.

The training of the machine learning model, in some embodiments, uses data from a protein database that is either internal to a provider network (protein database 104) or external to the provider network (110). In some embodiments, this database is the Structural Classification of Proteins-extended (SCOPe) database which is a curated database of protein structures annotated by protein fold. Models of identical architecture are trained on individual SCOPe classes. The primary sequence and Cartesian coordinates of the backbone heavy atoms typically serve as the model input. In some embodiments, all sidechain atoms are omitted.

In some embodiments, regardless of the architecture, the model is trained using a multi-task loss function for both sequence and structure recovery. Cross-entropy loss over the ablated region is used to train the network to perform sequence recovery. To train the network to perform structure recovery, a L1 loss function of the C-alpha distance matrix of the entire protein structure is used. Because the L1 loss calculated over the distance matrix is orders of magnitude than the cross entropy loss in our multi-task loss function, in some embodiments, the calculated L1 loss is scaled by the ratio of the cross entropy and L1 loss every thousand iterations.

In some embodiments, the total loss is the sum of two terms $\mathcal{L} = \mathcal{L}_{seq} + \mathcal{L}_{struct}$, where $$\mathcal{L}_{seq} = \left\langle \frac{1}{L} \sum_{\alpha=1}^{21} \sum_{j=1}^{L} p_{\alpha,j} \log(1 - \hat{p}_{\alpha,j}) \right\rangle d \in D,$$

and $$\mathcal{L}_{struct} = \left\langle \frac{1}{L^2} \sum_{i,j=1}^{L} |d_{ij} - \hat{d}_{ij}| \right\rangle d \in D,$$

Where L is the length of the protein, $p_{\alpha,j}$ is the predicated probability of the $\alpha^{th}$ amino acid at the $j^{th}$ residue in the protein sequence with normalization $\Sigma_\alpha p_{\alpha,j}=1$ for each j, $d_{ij}$ is the Euclidean distance between the predicted coordinate of the $C_\alpha$ backbone atom of the amino acid at the $i^{th}$ and $j^{th}$ residues in the protein sequence. Hats on the variables indicate the ground truth, observed values. The empirical expectation over the data D via mini-batch optimization is taken.

A provider network 100 (or, "cloud" provider network) provides users with the ability to utilize one or more of a variety of types of computing-related resources such as compute resources (e.g., executing virtual machine (VM) instances and/or containers, executing batch jobs, executing code without provisioning servers), data/storage resources (e.g., object storage, block-level storage, data archival storage, databases and database tables, etc.), network-related resources (e.g., configuring virtual networks including groups of compute resources, content delivery networks (CDNs), Domain Name Service (DNS)), application resources (e.g., databases, application build/deployment services), access policies or roles, identity policies or roles, machine images, routers and other data processing resources, etc. These and other computing resources may be provided as services, such as a hardware virtualization service that can execute compute instances, a storage service that can store data objects, etc. The users (or "customers") of provider networks 100 may utilize one or more user accounts that are associated with a customer account, though these terms may be used somewhat interchangeably depending upon the context of use. Users may interact with a provider network 100 across one or more intermediate networks 106 (e.g., the internet) via one or more interface(s), such as through use of application programming interface (API) calls, via a console implemented as a website or application, etc. An API refers to an interface and/or communication protocol between a client and a server, such that if the client makes a request in a predefined format, the client should receive a response in a specific format or initiate a defined action. In the cloud provider network context, APIs provide a gateway for customers to access cloud infrastructure by allowing customers to obtain data from or cause actions within the cloud provider network, enabling the development of applications that interact with resources and services hosted in the cloud provider network. APIs can also enable different services of the cloud provider network to exchange data with one another. The interface(s) may be part of, or serve as a front-end to, a control plane of the provider network 100 that includes "backend" services supporting and enabling the services that may be more directly offered to customers.

For example, a cloud provider network (or just "cloud") typically refers to a large pool of accessible virtualized computing resources (such as compute, storage, and networking resources, applications, and services). A cloud can provide convenient, on-demand network access to a shared pool of configurable computing resources that can be programmatically provisioned and released in response to customer commands. These resources can be dynamically provisioned and reconfigured to adjust to variable load. Cloud computing can thus be considered as both the applications delivered as services over a publicly accessible network (e.g., the Internet, a cellular communication network) and the hardware and software in cloud provider data centers that provide those services.

To provide these and other computing resource services, provider networks 100 often rely upon virtualization techniques. For example, virtualization technologies may be used to provide users the ability to control or utilize compute instances (e.g., a VM using a guest operating system (O/S) that operates using a hypervisor that may or may not further operate on top of an underlying host O/S, a container that may or may not operate in a VM, an instance that can execute on "bare metal" hardware without an underlying hypervisor), where one or multiple compute instances can be implemented using a single electronic device. Thus, a user may directly utilize a compute instance (e.g., provided by a hardware virtualization service) hosted by the provider network to perform a variety of computing tasks. Additionally, or alternatively, a user may indirectly utilize a compute instance by submitting code to be executed by the provider network (e.g., via an on-demand code execution service), which in turn utilizes a compute instance to execute the code typically without the user having any control of or knowledge of the underlying compute instance(s) involved.

For example, in various embodiments, a "serverless" function may include code provided by a user or other entity—such as the provider network itself—that can be executed on demand Serverless functions may be maintained within provider network 100 by an on-demand code execution service and may be associated with a particular user or account or be generally accessible to multiple users/accounts. A serverless function may be associated with a Uniform Resource Locator (URL), Uniform Resource Identifier (URI), or other reference, which may be used to invoke the serverless function. A serverless function may be executed by a compute instance, such as a virtual machine, container, etc., when triggered or invoked. In some embodiments, a serverless function can be invoked through an application programming interface (API) call or a specially formatted HyperText Transport Protocol (HTTP) request message. Accordingly, users can define serverless functions that can be executed on demand, without requiring the user to maintain dedicated infrastructure to execute the serverless function. Instead, the serverless functions can be executed on demand using resources maintained by the provider network 100. In some embodiments, these resources may be maintained in a "ready" state (e.g., having a pre-initialized runtime environment configured to execute the serverless functions), allowing the serverless functions to be executed in near real-time.

In some embodiments, a 3-D modeler 108 allows for a predicted pair to have a 3-D representation generated.

Circles with numbers in them indicate an exemplary flow using the protein sequence predictor 102. A circle 1, an edge device 112 sends a request for a prediction of a missing area of a protein's primary sequence and a corresponding 3-D position of the missing area. The protein sequence predictor 102 processes this request at circle 2. In this example, a 3-D representation is generated from the predication at circle 3.

The predication and 3-D representation are returned to the requester at circle 4.

Figure 2:
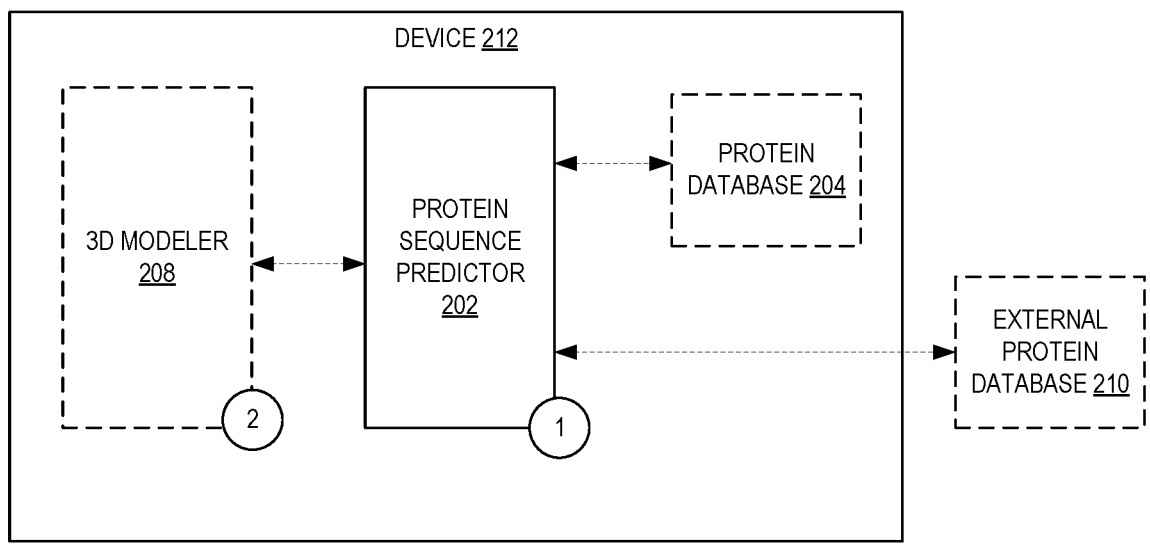
FIG. 2 illustrates embodiments of a device to predict missing areas of a protein's primary sequence and its corresponding three-dimensional position.

FIG. 2 illustrates embodiments of a device 212 to predict missing areas of a protein's primary sequence and its corresponding three-dimensional position. As shown, a protein sequence predictor 202 predicts using a machine learning model, according to a request, a protein sequence and coordinates of an ablated region. In some embodiments, the request includes a representation of protein primary sequence, backbone Cartesian coordinates for the primary sequence, and an indication of ablations (and/or, in some instances, regions of missing electron density) within the primary sequence. In some embodiments, the output of the protein sequence predictor 202 is a probability of each of the twenty amino acids as well as heavy atom backbone coordinates.

In some embodiments, the regions of ablation may be a set of mask tokens. Of course, other means of indicating a length of an ablated region may be used. Note that during training, the length of a location of an ablated region is varied with model iterations.

In some embodiments, an embedding of the machine learning model embeds the protein primary sequence into a high dimensional space. In some embodiments, the primary sequence is represented as 21 unique integers with a single integer representing noncanonical amino acids. The sequence is embedded into a higher dimensional space to allow for the expression of shared properties between the amino acids.

Additionally, in some embodiments, the Cartesian coordinates of the primary sequence are processed through a layer of convolutions to capture features distant in sequence space. For example, the coordinates to the center of mass of the protein may be centered and scaled by the radius of gyration of the structure to make the network more robust to structures of varying size. The embedded sequence and processed coordinates are combined (e.g., concatenated in some instances).

Following the combining of embedded sequence and processed coordinates are one or more layers. In some embodiments, an attention-based (such as a transformer-based) architecture is used. In this architecture, the combined embedded sequence and processed coordinates are added to a sinusoidal positional encoding. Then self-attention is calculated on this combined representation of the proteins sequence and structure via a multi-layer attention encoder and the final attended sequence and structure is passed through a final convolutional layer to predict the sequence and coordinates of the ablated region. The final output is the probability of each of the twenty amino acids as well as heavy atom backbone coordinates.

In some embodiments, the protein sequence predictor 202 is a convolution-based model. For example, the combined embedded sequence and processed coordinates are provided to a sequence of residual convolutional blocks to perform convolutions of a set channel dimension with a final position-independent, linear projection output from a fully connected network as a probability of each of the twenty amino acids as well as heavy atom backbone coordinates.

In some embodiments, the protein sequence predictor 202 is a bidirectional long short term memory (BiLSTM)-based model. For example, the combined embedded sequence and processed coordinates are provided to a multi-layer BiLSTM network, each LSTM of which has a plurality (e.g., 150) dimensional hidden channels. A final position-independent, linear projection using a fully-connected layer provides the output which is the probability of each of the twenty amino acids as well as heavy atom backbone coordinates.

In some embodiments, the request includes already combined embedded sequence and processed coordinates which are then fed into a BiLSTM-based architecture, an attention-based encoder, or convolutional neural network (CNN)-based architecture.

The training of the machine learning model, in some embodiments, uses data from an internal protein database 204 or external database 210. In some embodiments, this database is the Structural Classification of Proteins-extended (SCOPe) database which is a curated database of protein structures annotated by protein fold. Models of identical architecture are trained on individual SCOPe classes. The primary sequence and Cartesian coordinates of the backbone heavy atoms typically serve as the model input. In some embodiments, all sidechain atoms are omitted.

In some embodiments, regardless of the architecture, the model is trained using a multi-task loss function for both sequence and structure recovery. Cross-entropy loss over the ablated region is used to train the network to perform sequence recovery. To train the network to perform structure recovery, a L1 loss function of the C-alpha distance matrix of the entire protein structure is used. Because the L1 loss calculated over the distance matrix is orders of magnitude than the cross entropy loss in our multi-task loss function, in some embodiments, the calculated L1 loss is scaled by the ratio of the cross entropy and L1 loss every thousand iterations.

In some embodiments, the total loss is the sum of two terms $\mathcal{L} = \mathcal{L}_{seq} + \mathcal{L}_{struct}$, where $$\mathcal{L}_{seq} = \left\{ \frac{1}{L} \sum_{\alpha=1}^{21} \sum_{j=1}^{L} p_{\alpha,j} \log(1 - \hat{p}_{\alpha,j}) \right\} d \in D,$$

and $$\mathcal{L}_{struct} = \left\{ \frac{1}{L^2} \sum_{i,j=1}^{L} |d_{ij} - \hat{d}_{ij}| \right\} d \in D,$$

Where L is the length of the protein, $p_{\alpha,j}$ is the predicated probability of the $\alpha^{th}$ amino acid at the $j^{th}$ residue in the protein sequence with normalization $\Sigma_\alpha p_{\alpha,j}=1$ for each j, $d_{ij}$ is the Euclidean distance between the predicted coordinate of the C a backbone atom of the amino acid at the $i^{th}$ and $j^{th}$ residues in the protein sequence. Hats on the variables indicate the ground truth, observed values. The empirical expectation over the data D via mini-batch optimization is taken.

In some embodiments, a 3-D modeler 208 allows for a predicted pair to have a 3-D representation generated.

Circles with numbers in them indicate an exemplary flow using the protein sequence predictor 202. A circle 1, a request for a prediction of a missing area of a protein's primary sequence and a corresponding 3-D position of the missing area is processed by the sequence predictor 202. A 3-D representation is generated from the predication at circle 2.

Proteins are built from twenty-one different amino acids arranged in a particular order. The order of the amino acids in the protein is the primary structure of the protein. Each amino acid shares a common set of atoms that make up the amino acid common backbone. Attached to the central carbon atom ("carbon alpha") is an atom or group of atoms that varies among the amino acids, making them all different. This group may be referred to as the R group or an amino acid sidechain. The twenty-one amino acids found in proteins only vary in their R groups or sidechains. These functional groups provide unique properties important both in the way proteins fold and in the way proteins function.

Figure 3:
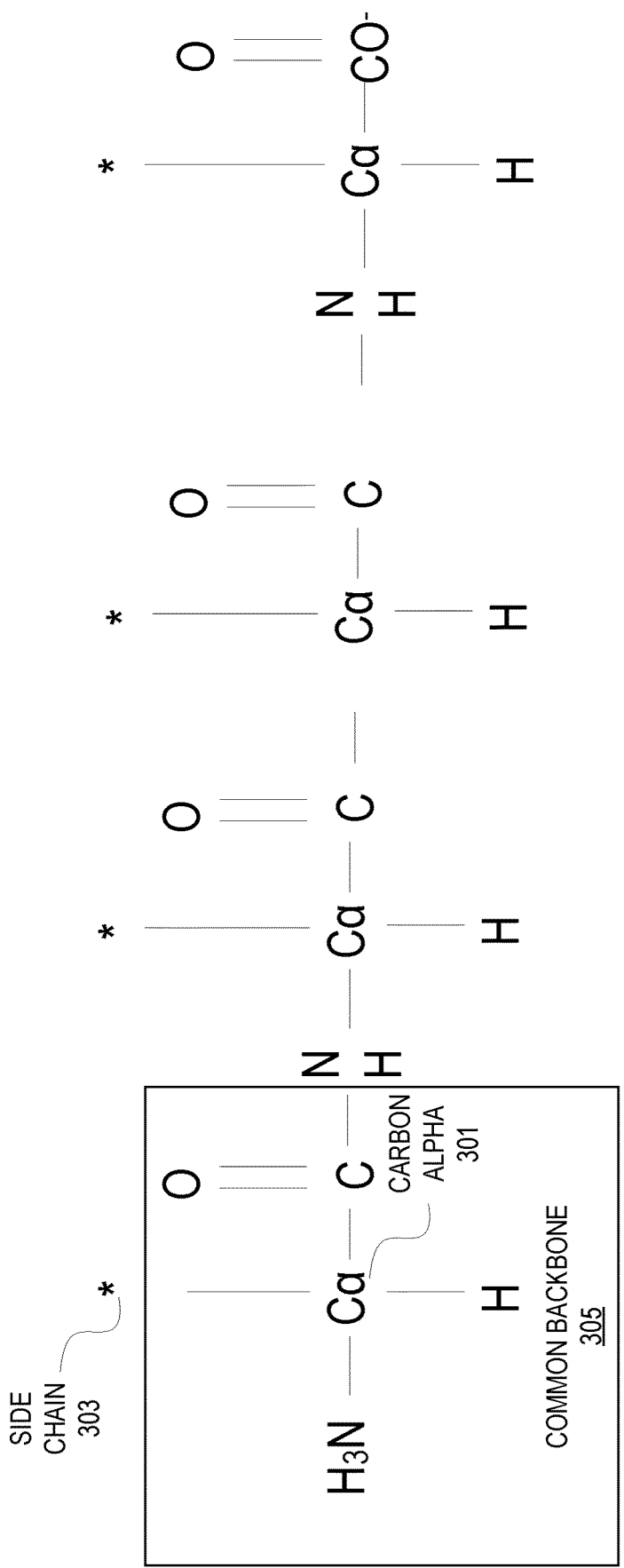
FIG. 3 illustrates an amino acid.

FIG. 3 illustrates an example of an amino acid residue. The common backbone 305 includes an amino group ($NH_3$) that is positively charged and the carboxyl group (COO—) is negatively charged. The carbon atom between these groups is the carbon alpha atom 301. In a protein, the chemical properties of each sidechain 303 are the major determinant of the final, folded 3-D structure.

In some embodiments, the amino acids of the chain are represented using one-letter amino acid codes or their three-letter equivalents. Table I below illustrates an example of amino acid representations that conform to International Union of Pure and Applied Chemistry usage.

TABLE I

| Symbol | 3-letter | Meaning | Codons | IUB Depiction | |
|---|---|---|---|---|---|
| A | Ala | Alanine | GCT, GCC, GCA, GCG | !GCX | |
| B | Asp, Asn | Aspartic, Asparagine | GAT, GAC, AAT, AAC | | !RAY |
| C | Cys | Cysteine | TGT, TGC | !TGY | |
| D | Asp | Aspartic | GAT, GAC | !GAY | |
| E | Glu | Glutamic | GAA, GAG | !GAR | |
| F | Phe | Phenylalanine | TTT, TTC | !TTY | |
| G | Gly | Glycine | GGT, GGC, GGA, GGG | | !GGX |
| H | His | Histidine | CAT, CAC | | !CAY |
| I | Ile | Isoleucine | ATT, ATC, ATA | | !ATH |
| K | Lys | Lysine | AAA, AAG | !AAR | |
| L | Leu | Leucine | TTG, TTA, CTT, CTC, CTA, CTG !TTR, CTX, YTR; YTX | | |
| M | Met | Methionine | ATG | !ATG | |
| N | Asn | Asparagine | AAT, AAC | !AAY | |
| P | Pro | Proline | CCT, CCC, CCA, CCG | !CCX | |
| Q | Gln | Glutamine | CAA, CAG | !CAR | |
| R | Arg | Arginine | CGT, CGC, CGA, CGG, AGA, AGG !CGX, AGR, MGR; MGX | | |
| S | Ser | Serine | TCT, TCC, TCA, TCG, AGT, AGC | | !TCX, AGY; WSX |
| T | Thr | Threonine | ACT, ACC, ACA, ACG | !ACX | |
| V | Val | Valine | GTT, GTC, GTA, GTG | !GTX | |
| W | Trp | Tryptophan | TGG | !TGG | |
| X | Xxx | Unknown | | !XXX | |

TABLE I-continued

| Symbol | 3-letter | Meaning | Codons | IUB Depiction | |
|---|---|---|---|---|---|
| Y | Tyr | Tyrosine | TAT, TAC | !TAY | |
| Z | Glu, Gln | Glutamic, Glutamine | GAA, GAG, CAA, CAG | !SAR | |
| * | End | Terminator | TAA, TAG, TGA | | !TAR, TRA; TRR |

Figure 4:
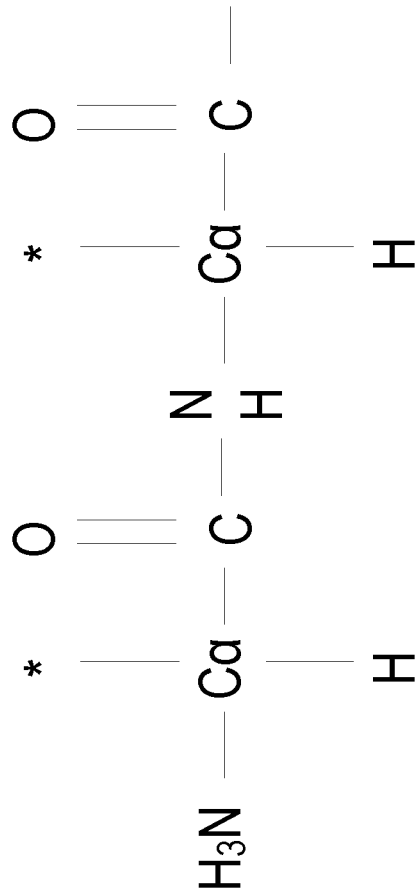
FIG. 4 illustrates an example of a protein comprised of a plurality of amino acids with an ablated area.
Figure 4:
Figure 4:
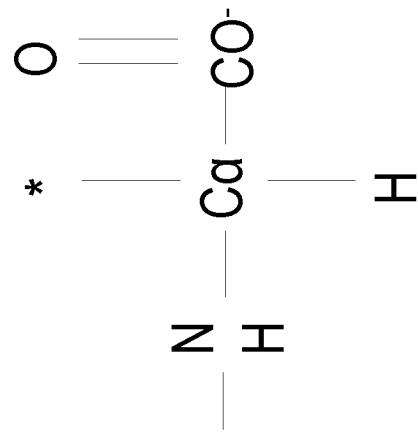

FIG. 4 illustrates an example of a protein residue comprised of a plurality of amino acids with an ablated area. The primary structure of a protein is the linear sequence of amino acids joined together by peptide bonds. As noted above, amino acids consist of a common backbone (which allows them to be joined together in any order) and a variable sidechain group, which impacts both the final protein structure and its function.

A primary structure of a protein is the amino acid sequence of the protein. A secondary structure of a protein refers to the alpha helices or beta sheets in the protein. These two common secondary structural elements are stabilized by hydrogen bonding between backbone atoms (the side chains are not involved in protein secondary structure). A tertiary structure of a protein refers to the overall 3D folded structure of a protein. A quaternary structure of a protein refers to protein complexes composed of more than one protein chain. Although some proteins exist as monomers (and therefore have no quaternary structure), many proteins interact to form multi-component protein complexes.

In this example, the chain of amino acids has an ablated (missing) area 401 which a machine learning model of the protein sequence predictor service 102 or protein sequence predictor 202 is to predict.

Figure 5:
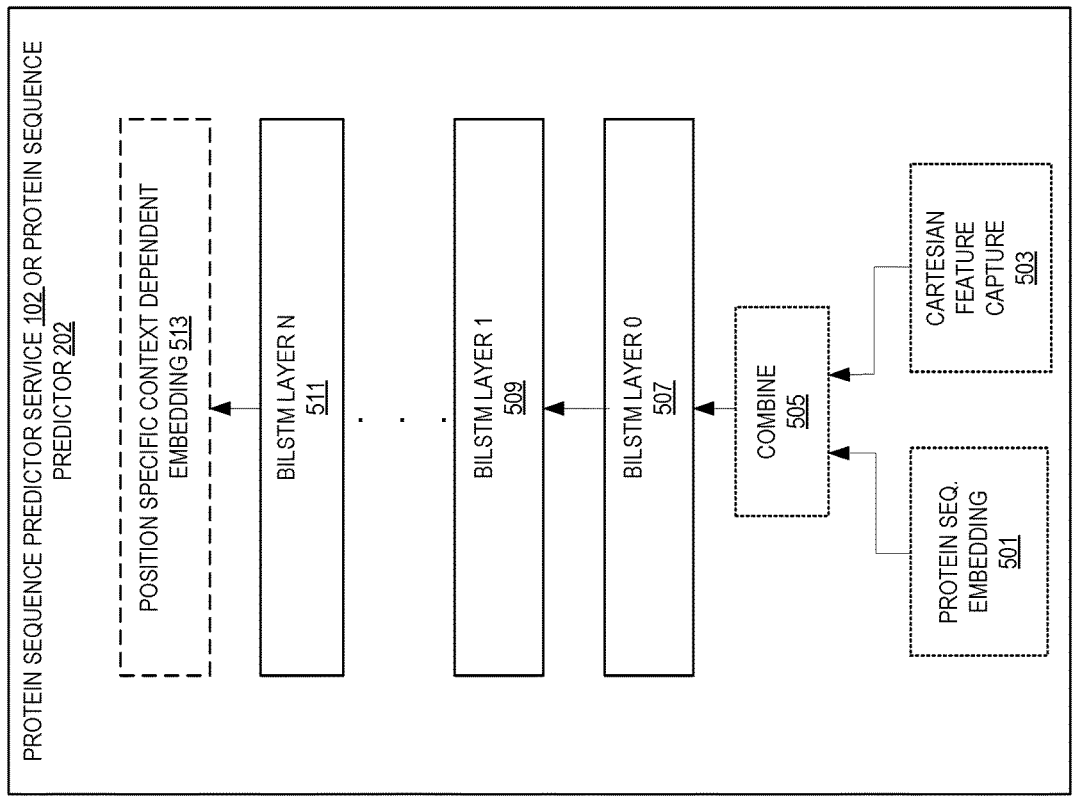
FIG. 5 illustrates embodiments of a machine learning model of a protein sequence predictor service or protein sequence predictor that utilizes LSTM.

FIG. 5 illustrates embodiments of a machine learning model of a protein sequence predictor service or protein sequence predictor that utilizes LSTM. For example, this illustration represents aspects of the protein sequence predictor service 102 or protein sequence predictor 202.

As noted above, request to the protein sequence predictor service 102 or protein sequence predictor typically includes a protein primary sequence, backbone Cartesian coordinates for the primary sequence, and an indication of ablations (and/or, in some instances, regions of missing electron density) within the primary sequence. An embedding 501 embeds the input protein primary sequence into a high dimensional space. In some embodiments, the primary sequence is represented as 21 unique integers with a single integer representing noncanonical amino acids.

The backbone Cartesian coordinates of the primary sequence are captured using Cartesian feature capture block 503. For example, in some embodiments, the backbone Cartesian coordinates are processed through a layer of convolutions to capture features distant in sequence space. For example, the coordinates to the center of mass of the protein may be centered and scaled by the radius of gyration of the structure to make the network more robust to structures of varying size.

In some embodiments, the embedded sequence and processed coordinates are combined (e.g., concatenated in some instances) at a combine block 505. Note that this may not be done depending on how the model has been trained. Further, the embedding, Cartesian feature capture, and/or combination may be done outside of the protein sequence predictor service 102 or protein sequence predictor 202. As such, the input to the machine learning model may just be the embedded sequence and captured Cartesian coordinates.

Regardless, the input to the BiLSTM layer 0 507 includes the embedded sequence and captured Cartesian coordinates. Each of the BiLSTM layers (BiLSTM layer 0 507, BiLSTM layer 509, and BiLSTM layer N 511) has a plurality of dimensional hidden channels. While three layers are shown, the "N" in BiLSTM layer N 511 indicates that the number of BiLSTM layers may vary. There may be 1, 2, 3, etc. In some embodiments, there is a dropout of a set percentage after each BiLSTM layer.

In some embodiments, a position specific context dependent embedding 513 is applied to the output of the BiLSTM processing and generates a final position-independent, linear projection into a plurality of dimensions which represents the missing areas of a protein's primary sequence and its corresponding three-dimensional position based off of a known residue and position of the remaining amino acids in the protein using one or more machine learning models. In some embodiments, there are 21 dimensions for the amino acids, 1 for padding, and 3 for the Cartesian backbone. Examples of a position specific context dependent embedding include, but are not limited to, a fully-connected network.

Figure 6:
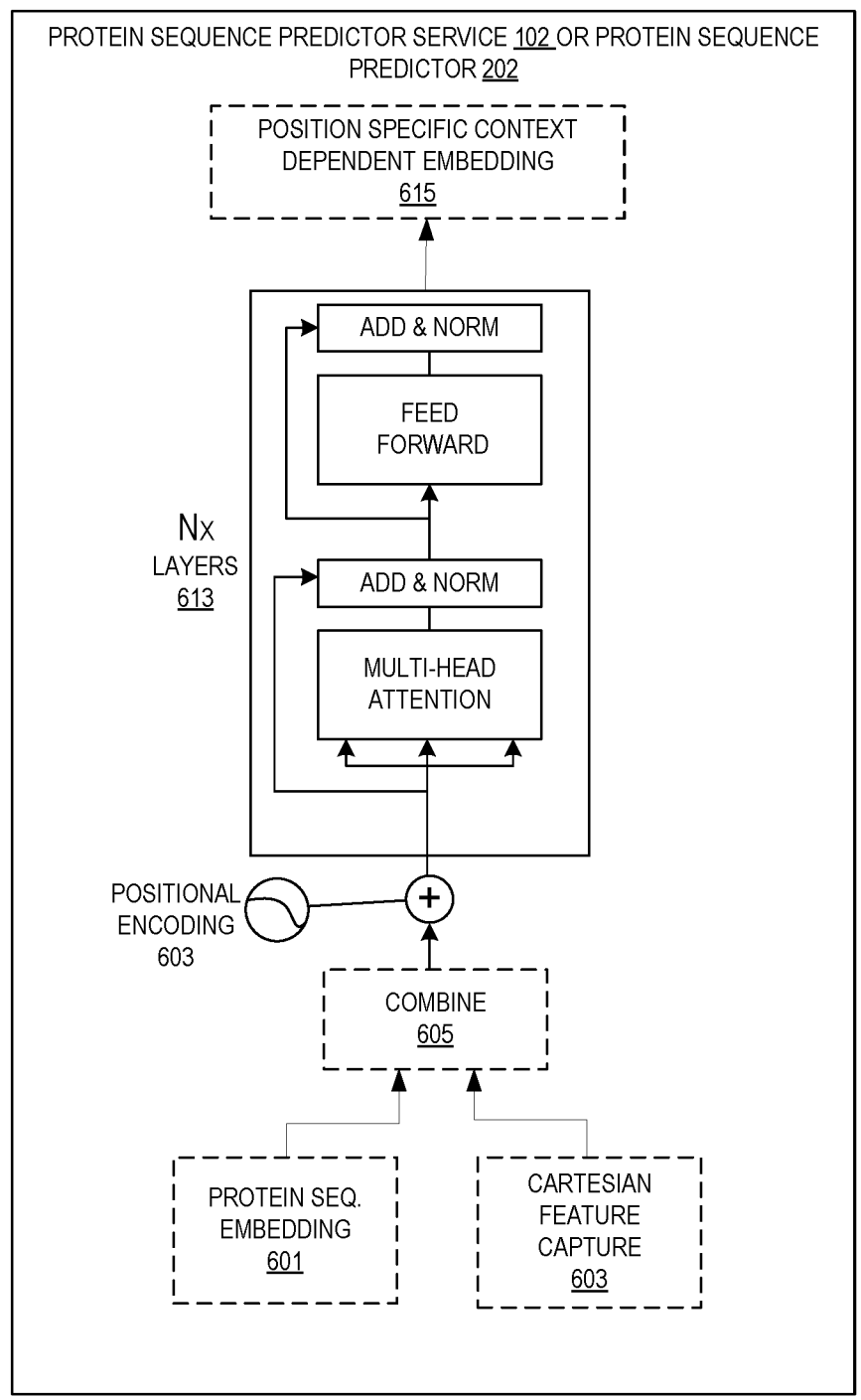
FIG. 6 illustrates embodiments of a machine learning model of a protein sequence predictor service or protein sequence predictor that utilizes an attention-based model.

FIG. 6 illustrates embodiments of a machine learning model of a protein sequence predictor service or protein sequence predictor that utilizes an attention-based model. For example, this illustration represents aspects of the protein sequence predictor service 102 or protein sequence predictor 202.

As noted above, request to the protein sequence predictor service 102 or protein sequence predictor typically includes a protein primary sequence, backbone Cartesian coordinates for the primary sequence, and an indication of ablations (and/or, in some instances, regions of missing electron density) within the primary sequence. An embedding 601 embeds the input protein primary sequence into a high dimensional space. In some embodiments, the primary sequence is represented as 21 unique integers with a single integer representing noncanonical amino acids.

The backbone Cartesian coordinates of the primary sequence are captured using Cartesian feature capture block 603. For example, in some embodiments, the backbone Cartesian coordinates are processed through a layer of convolutions to capture features distant in sequence space. For example, the coordinates to the center of mass of the protein may be centered and scaled by the radius of gyration of the structure to make the network more robust to structures of varying size.

In some embodiments, the embedded sequence and processed coordinates are combined (e.g., concatenated in some instances) at a combine block 605. Note that this may not be done depending on how the model has been trained. Further, the embedding, Cartesian feature capture, and/or combination may be done outside of the protein sequence predictor service 102 or protein sequence predictor 202. As such, the input to the machine learning model may just be the embedded sequence and captured Cartesian coordinates.

As shown, an input embedding 601 is applied to the embedded sequence and captured Cartesian coordinates along with and added a positional encoding 603. In some embodiments, the embedding dimension is 10 and the positional encoding has a dimension of 192.

The model is composed of a stack of N (e.g., 4) identical layers 613 with each layer having multiple sub-layers. In some embodiments, the sub-layers have a hidden dimension size that corresponds to the positional encoding dimension size. In some embodiments, a first sub-layer is a multi-head self-attention mechanism, and a subsequent layer is a position-wise fully connected feed-forward network. A residual connection is around each of the sub-layers, followed by layer normalization.

In some embodiments, the output of the N layers is subjected to a position specific context dependent embedding 615 and generates a final position-independent, linear projection into a plurality of dimensions which represents the missing areas of a protein's primary sequence and its corresponding three-dimensional position based off of a known residue and position of the remaining amino acids in the protein using one or more machine learning models. In some embodiments, there are 21 dimensions for the amino acids, 1 for padding, and 3 for the Cartesian backbone. Examples of a position specific context dependent embedding include, but are not limited to, a fully-connected network.

Figure 7:
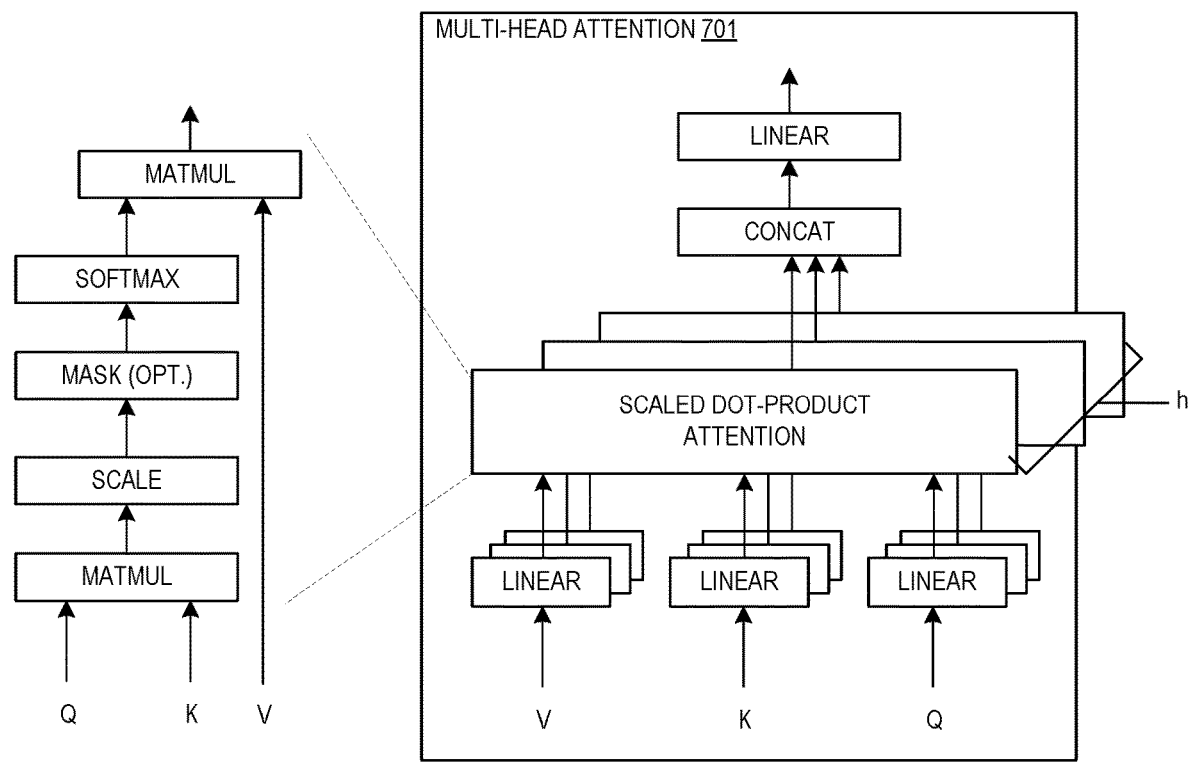
FIG. 7 illustrates embodiments of the multi-headed attention mechanism of the encoder of FIG. 6.

FIG. 7 illustrates embodiments of the multi-headed attention mechanism of the encoder of FIG. 6. This example of multi-headed attention uses a "Scaled Dot-Product Attention" (highlighted on the left). The input of the scaled dot-product attention which is defined as:

$$\text{Attention}(Q, K, V) = \text{softmax}\left(\frac{QK^T}{\sqrt{dk}}\right)$$

Q is a matrix that contains the query (vector representation of one word in the sequence), K are all the keys (vector representations of all the words in the sequence) and V are the values, which are again the vector representations of all the words in the sequence. For the encoder and decoder, multi-head attention modules, V consists of the same word sequence than Q. However, for the attention module that is considering the encoder and the decoder sequences, V is different from the sequence represented by Q.

The multi-head attention 701 divides the input vector into chunks and then the scalar dot-product attention is applied on each chunk in parallel. Finally, the average of all the chunk outputs is computed.

Figure 8:
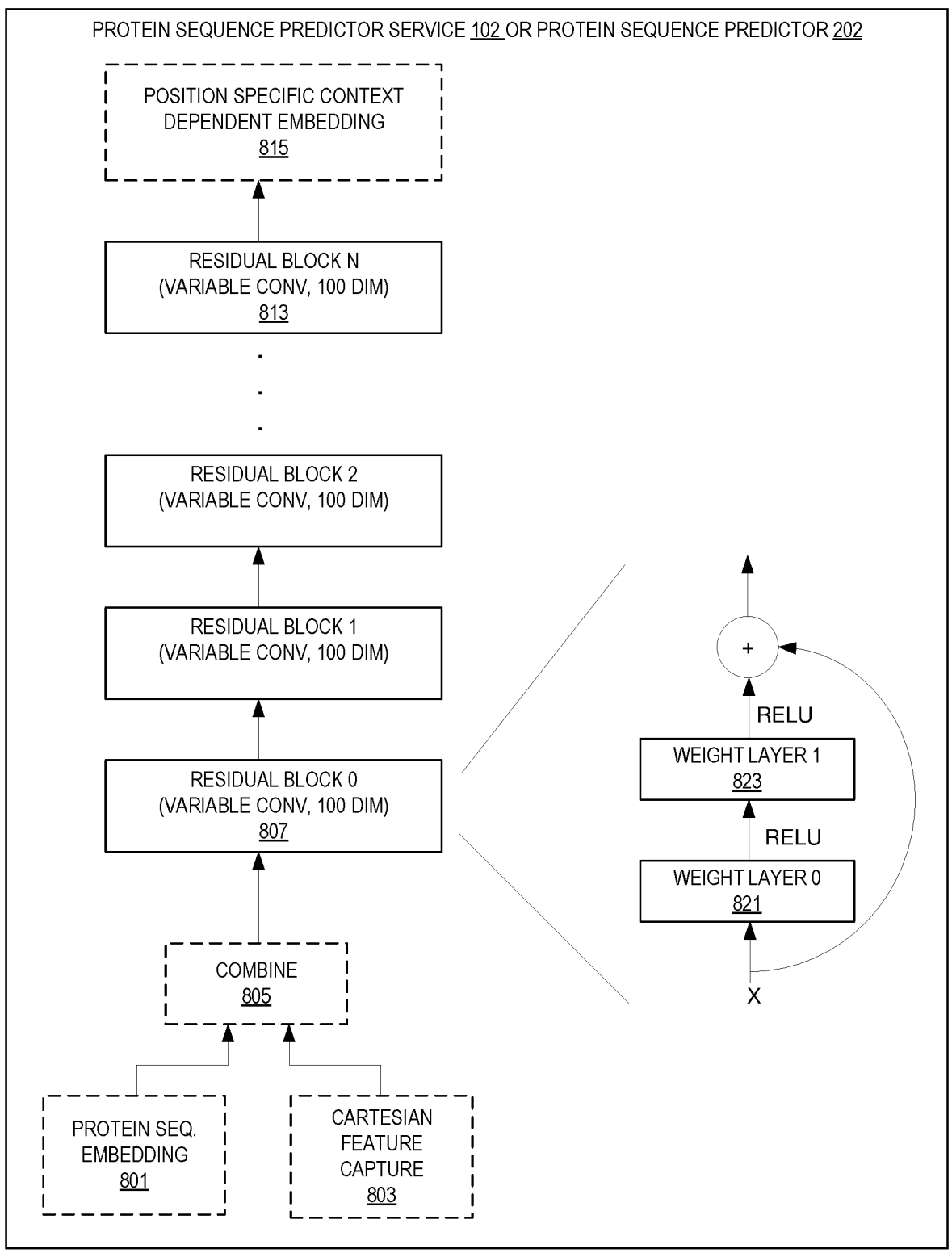
FIG. 8 illustrates embodiments of a machine learning model of a protein sequence predictor service or protein sequence predictor that utilizes a convolutional-based model.

FIG. 8 illustrates embodiments of a machine learning model of a protein sequence predictor service or protein sequence predictor that utilizes a convolutional-based model. For example, this illustration represents aspects of the protein sequence predictor service 102 or protein sequence predictor 202.

In this example, a plurality of residual blocks is used. Each residual block has at least two convolutional layers (e.g., weight layer 0 821 and weight layer 1 821) with the same number of output channels (dimensions). Each convolutional layer is followed by a rectified linear unit (ReLU) activation function and in some instances a batch normalization layer. The two convolution operations are skipped, and the input added directly before the final ReLU activation function.

As noted above, request to the protein sequence predictor service 102 or protein sequence predictor typically includes a protein primary sequence, backbone Cartesian coordinates for the primary sequence, and an indication of ablations (and/or, in some instances, regions of missing electron density) within the primary sequence. An embedding 801 embeds the input protein primary sequence into a high dimensional space. In some embodiments, the primary sequence is represented as 21 unique integers with a single integer representing noncanonical amino acids.

The backbone Cartesian coordinates of the primary sequence are captured using Cartesian feature capture block 803. For example, in some embodiments, the backbone Cartesian coordinates are processed through a layer of convolutions to capture features distant in sequence space. For example, the coordinates to the center of mass of the protein may be centered and scaled by the radius of gyration of the structure to make the network more robust to structures of varying size.

In some embodiments, the embedded sequence and processed coordinates are combined (e.g., concatenated in some instances) at a combine block 805. Note that this may not be done depending on how the model has been trained. Further, the embedding, Cartesian feature capture, and/or combination may be done outside of the protein sequence predictor service 102 or protein sequence predictor 202. As such, the input to the machine learning model may just be the embedded sequence and captured Cartesian coordinates.

The embedded sequence and captured Cartesian coordinates are an input to a plurality of sequential, residual convolution blocks 0 to N 807-813. Each of the residual convolution blocks has a plurality (e.g., 100) of channel dimensions and a convolutional size that may vary depending on the implementation.

In some embodiments, the output of the N residual blocks is subjected to a position specific context dependent embedding 615 which generates a final position-independent, linear projection into a plurality of dimensions which represents the missing areas of a protein's primary sequence and its corresponding three-dimensional position based off of a known residue and position of the remaining amino acids in the protein using one or more machine learning models. In some embodiments, there are 21 dimensions for the amino acids, 1 for padding, and 3 for the Cartesian backbone. Examples of a position specific context dependent embedding include, but are not limited to, a fully-connected network.

In some embodiments, there are 21 dimensions for the amino acids, 1 for padding, and 3 for the Cartesian backbone. Examples of a position specific context dependent embedding include, but are not limited to, a fully-connected network.

Figure 9:
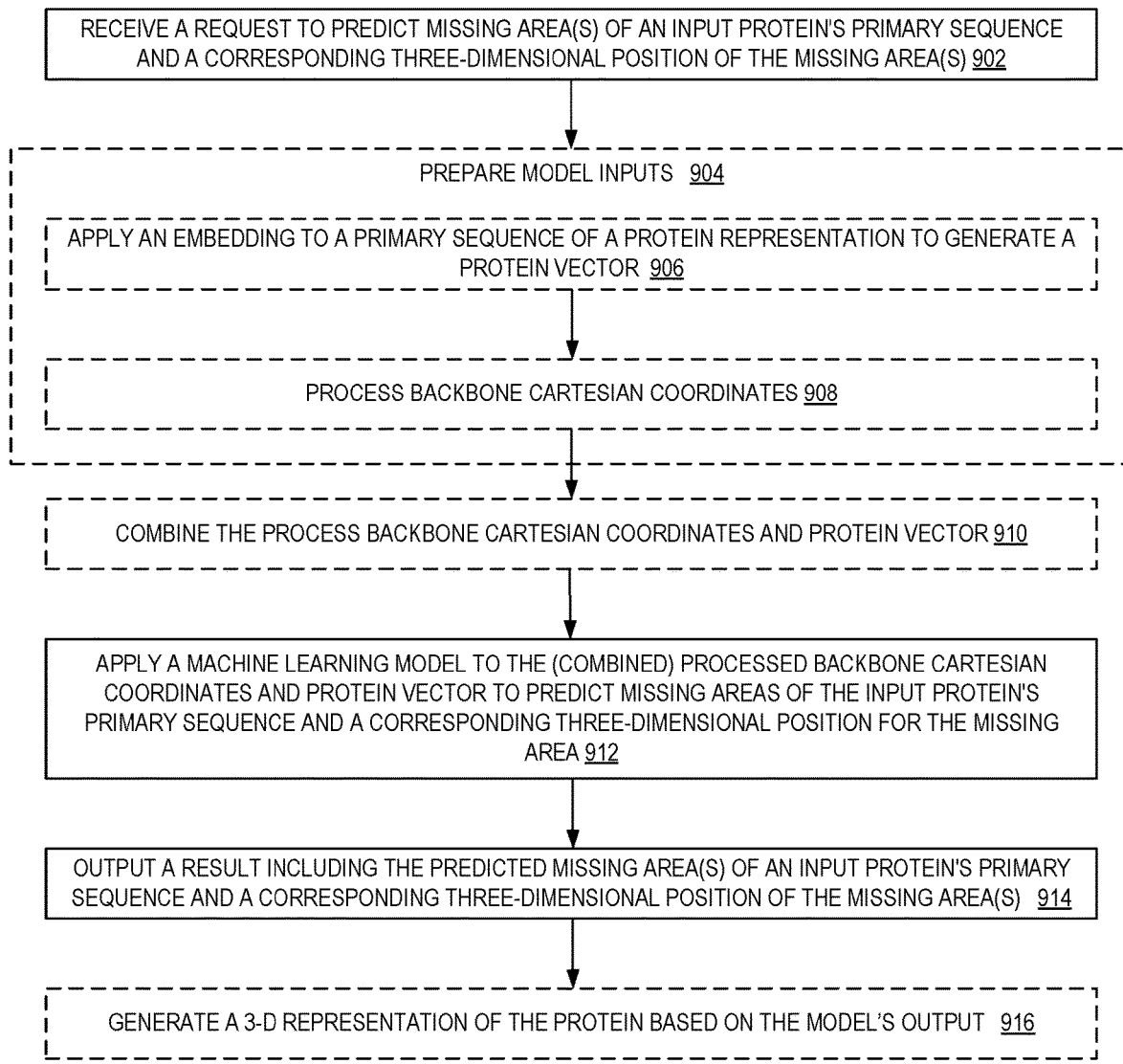
FIG. 9 is a flow diagram illustrating operations of a method for predicting a missing area of a protein and its corresponding 3-D position.

FIG. 9 is a flow diagram illustrating operations of a method for predicting a missing area of a protein and its corresponding 3-D position. Some or all of the operations (or other processes described herein, or variations, and/or combinations thereof) are performed under the control of one or more computer systems configured with executable instructions and are implemented as code (e.g., executable instructions, one or more computer programs, or one or more applications) executing collectively on one or more processors, by hardware or combinations thereof. The code is stored on a computer-readable storage medium, for example, in the form of a computer program comprising instructions executable by one or more processors. The computer-readable storage medium is non-transitory. In some embodiments, one or more (or all) of the operations are performed by the protein sequence predictor 102 or enzyme-substrate predictor 202 of the other figures.

At 902, a request is received to predict missing areas of an input protein's primary sequence and a corresponding three-dimensional position of the missing area. As noted above, this request may include a representation of protein primary sequence, backbone Cartesian coordinates for the primary sequence, and an indication of ablations (and/or, in some instances, regions of missing electron density) within the primary sequence. In some embodiments, the request includes conditioned versions of that information. In some embodiments, the indication of regions of ablation may be a set of mask tokens in the protein primary sequence.

In some embodiments, the protein primary sequence, backbone Cartesian coordinates for the primary sequence, and an indication of ablations are conditioned (prepared) at 904. This preparation may include multiple acts depending on the implementation.

In some embodiments, an embedding is applied to the primary sequence of a protein representation to generate a protein vector at 906. In some embodiments, the backbone Cartesian coordinates processed to capture more features at 908. Note a longer discussion of how this may be done is detailed above.

Depending on how the underlying machine learning model has been trained, in some embodiments the processed backbone Cartesian coordinates and protein vector are combined at 910. For example, they are concatenated.

A machine learning model is applied to the (combined) processed backbone Cartesian coordinates and protein vector to predict missing areas of the input protein's primary sequence and a corresponding three-dimensional position for the missing area at 912. Note that the type of model is implementation dependent, but could be, for example, selected from a model that is LSTM-based, attention-based, CNN-based, etc.

A result including the predicted missing area(s) of an input protein's primary sequence and a corresponding three-dimensional position of the missing area(s) is output at 914.

In some embodiments, a 3-d representation of the protein is generated based on the output at 916.

Figure 10:
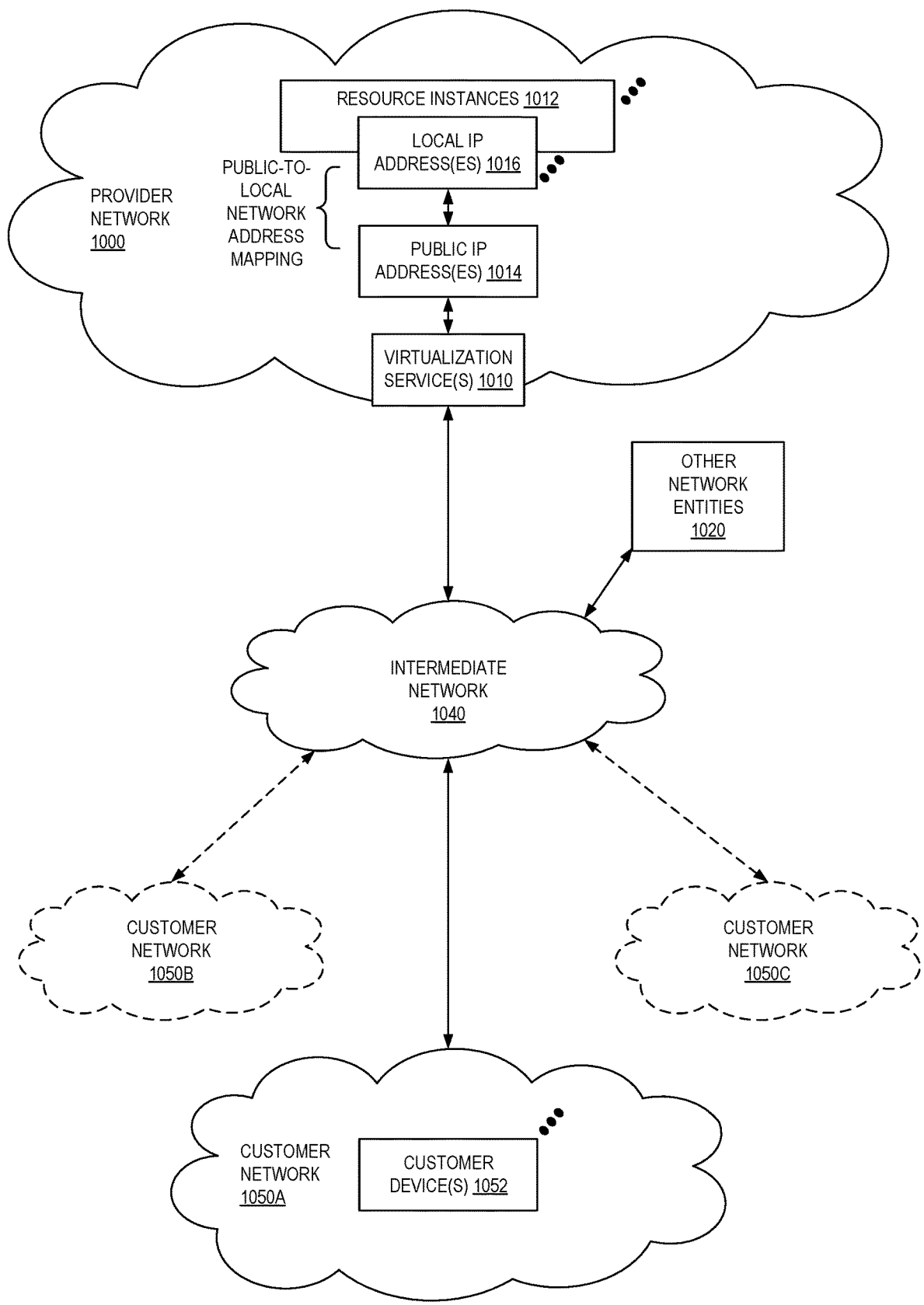
FIG. 10 illustrates an example provider network environment according to some embodiments.

FIG. 10 illustrates an example provider network (or "service provider system") environment according to some embodiments. A provider network 1000 may provide resource virtualization to customers via one or more virtualization services 1010 that allow customers to purchase, rent, or otherwise obtain instances 1012 of virtualized resources, including but not limited to computation and storage resources, implemented on devices within the provider network or networks in one or more data centers. Local Internet Protocol (IP) addresses 1016 may be associated with the resource instances 1012; the local IP addresses are the internal network addresses of the resource instances 1012 on the provider network 1000. In some embodiments, the provider network 1000 may also provide public IP addresses 1014 and/or public IP address ranges (e.g., Internet Protocol version 4 (IPv4) or Internet Protocol version 6 (IPv6) addresses) that customers may obtain from the provider 1000.

Conventionally, the provider network 1000, via the virtualization services 1010, may allow a customer of the service provider (e.g., a customer that operates one or more client networks 1050A-1050C including one or more customer device(s) 1052) to dynamically associate at least some public IP addresses 1014 assigned or allocated to the customer with particular resource instances 1012 assigned to the customer. The provider network 1000 may also allow the customer to remap a public IP address 1014, previously mapped to one virtualized computing resource instance 1012 allocated to the customer, to another virtualized computing resource instance 1012 that is also allocated to the customer. Using the virtualized computing resource instances 1012 and public IP addresses 1014 provided by the service provider, a customer of the service provider such as the operator of customer network(s) 1050A-1050C may, for example, implement customer-specific applications and present the customer's applications on an intermediate network 1040, such as the Internet. Other network entities 1020 on the intermediate network 1040 may then generate traffic to a destination public IP address 1014 published by the customer network(s) 1050A-1050C; the traffic is routed to the service provider data center, and at the data center is routed, via a network substrate, to the local IP address 1016 of the virtualized computing resource instance 1012 currently mapped to the destination public IP address 1014. Similarly, response traffic from the virtualized computing resource instance 1012 may be routed via the network substrate back onto the intermediate network 1040 to the source entity 1020.

Local IP addresses, as used herein, refer to the internal or "private" network addresses, for example, of resource instances in a provider network. Local IP addresses can be within address blocks reserved by Internet Engineering Task Force (IETF) Request for Comments (RFC) 1918 and/or of an address format specified by IETF RFC 4193 and may be mutable within the provider network. Network traffic originating outside the provider network is not directly routed to local IP addresses; instead, the traffic uses public IP addresses that are mapped to the local IP addresses of the resource instances. The provider network may include networking devices or appliances that provide network address translation (NAT) or similar functionality to perform the mapping from public IP addresses to local IP addresses and vice versa.

Public IP addresses are Internet mutable network addresses that are assigned to resource instances, either by the service provider or by the customer. Traffic routed to a public IP address is translated, for example via 1:1 NAT, and forwarded to the respective local IP address of a resource instance.

Some public IP addresses may be assigned by the provider network infrastructure to particular resource instances; these public IP addresses may be referred to as standard public IP addresses, or simply standard IP addresses. In some embodiments, the mapping of a standard IP address to a local IP address of a resource instance is the default launch configuration for all resource instance types.

At least some public IP addresses may be allocated to or obtained by customers of the provider network 1000; a customer may then assign their allocated public IP addresses to particular resource instances allocated to the customer. These public IP addresses may be referred to as customer public IP addresses, or simply customer IP addresses. Instead of being assigned by the provider network 1000 to resource instances as in the case of standard IP addresses, customer IP addresses may be assigned to resource instances by the customers, for example via an API provided by the service provider. Unlike standard IP addresses, customer IP addresses are allocated to customer accounts and can be remapped to other resource instances by the respective customers as necessary or desired. A customer IP address is associated with a customer's account, not a particular resource instance, and the customer controls that IP address until the customer chooses to release it. Unlike conventional static IP addresses, customer IP addresses allow the customer to mask resource instance or availability zone failures by remapping the customer's public IP addresses to any resource instance associated with the customer's account. The customer IP addresses, for example, enable a customer to engineer around problems with the customer's resource instances or software by remapping customer IP addresses to replacement resource instances.

Figure 11:
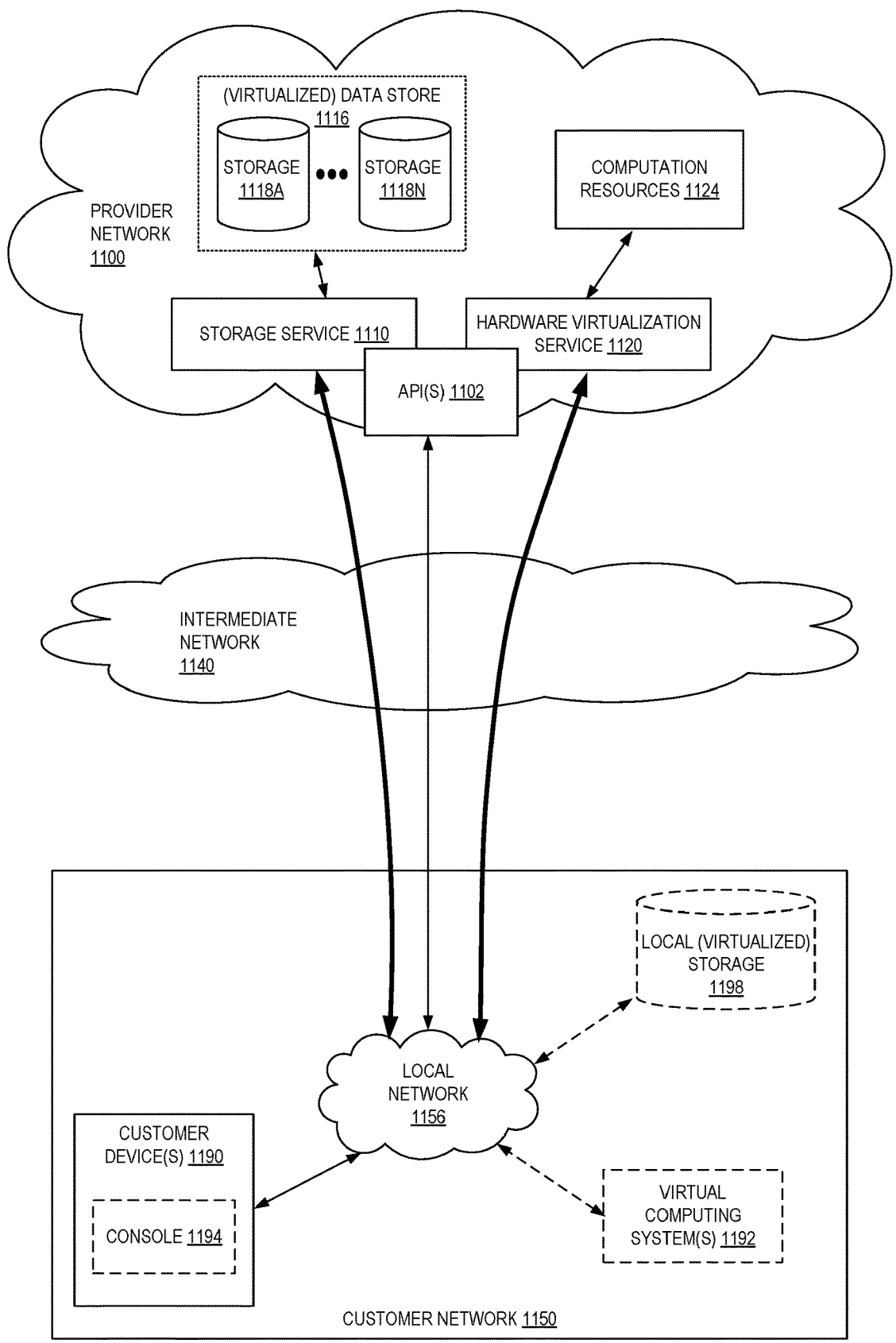
FIG. 11 is a block diagram of an example provider network that provides a storage service and a hardware virtualization service to customers according to some embodiments.

FIG. 11 is a block diagram of an example provider network that provides a storage service and a hardware virtualization service to customers, according to some embodiments. Hardware virtualization service 1120 provides multiple computation resources 1124 (e.g., VMs) to customers. The computation resources 1124 may, for example, be rented or leased to customers of the provider network 1100 (e.g., to a customer that implements customer network 1150). Each computation resource 1124 may be provided with one or more local IP addresses. Provider network 1100 may be configured to route packets from the local IP addresses of the computation resources 1124 to public Internet destinations, and from public Internet sources to the local IP addresses of computation resources 1124.

Provider network 1100 may provide a customer network 1150, for example coupled to intermediate network 1140 via local network 1156, the ability to implement virtual computing systems 1192 via hardware virtualization service 1120 coupled to intermediate network 1140 and to provider network 1100. In some embodiments, hardware virtualization service 1120 may provide one or more APIs 1102, for example a web services interface, via which a customer network 1150 may access functionality provided by the hardware virtualization service 1120, for example via a console 1194 (e.g., a web-based application, standalone application, mobile application, etc.). In some embodiments, at the provider network 1100, each virtual computing system 1192 at customer network 1150 may correspond to a computation resource 1124 that is leased, rented, or otherwise provided to customer network 1150.

From an instance of a virtual computing system 1192 and/or another customer device 1190 (e.g., via console 1194), the customer may access the functionality of storage service 1110, for example via one or more APIs 1102, to access data from and store data to storage resources 1118A-1118N of a virtual data store 1116 (e.g., a folder or "bucket", a virtualized volume, a database, etc.) provided by the provider network 1100. In some embodiments, a virtualized data store gateway (not shown) may be provided at the customer network 1150 that may locally cache at least some data, for example frequently-accessed or critical data, and that may communicate with storage service 1110 via one or more communications channels to upload new or modified data from a local cache so that the primary store of data (virtualized data store 1116) is maintained. In some embodiments, a user, via a virtual computing system 1192 and/or on another customer device 1190, may mount and access virtual data store 1116 volumes via storage service 1110 acting as a storage virtualization service, and these volumes may appear to the user as local (virtualized) storage 1198.

While not shown in FIG. 11, the virtualization service(s) may also be accessed from resource instances within the provider network 1100 via API(s) 1102. For example, a customer, appliance service provider, or other entity may access a virtualization service from within a respective virtual network on the provider network 1100 via an API 1102 to request allocation of one or more resource instances within the virtual network or within another virtual network.

Illustrative Systems

Figure 12:
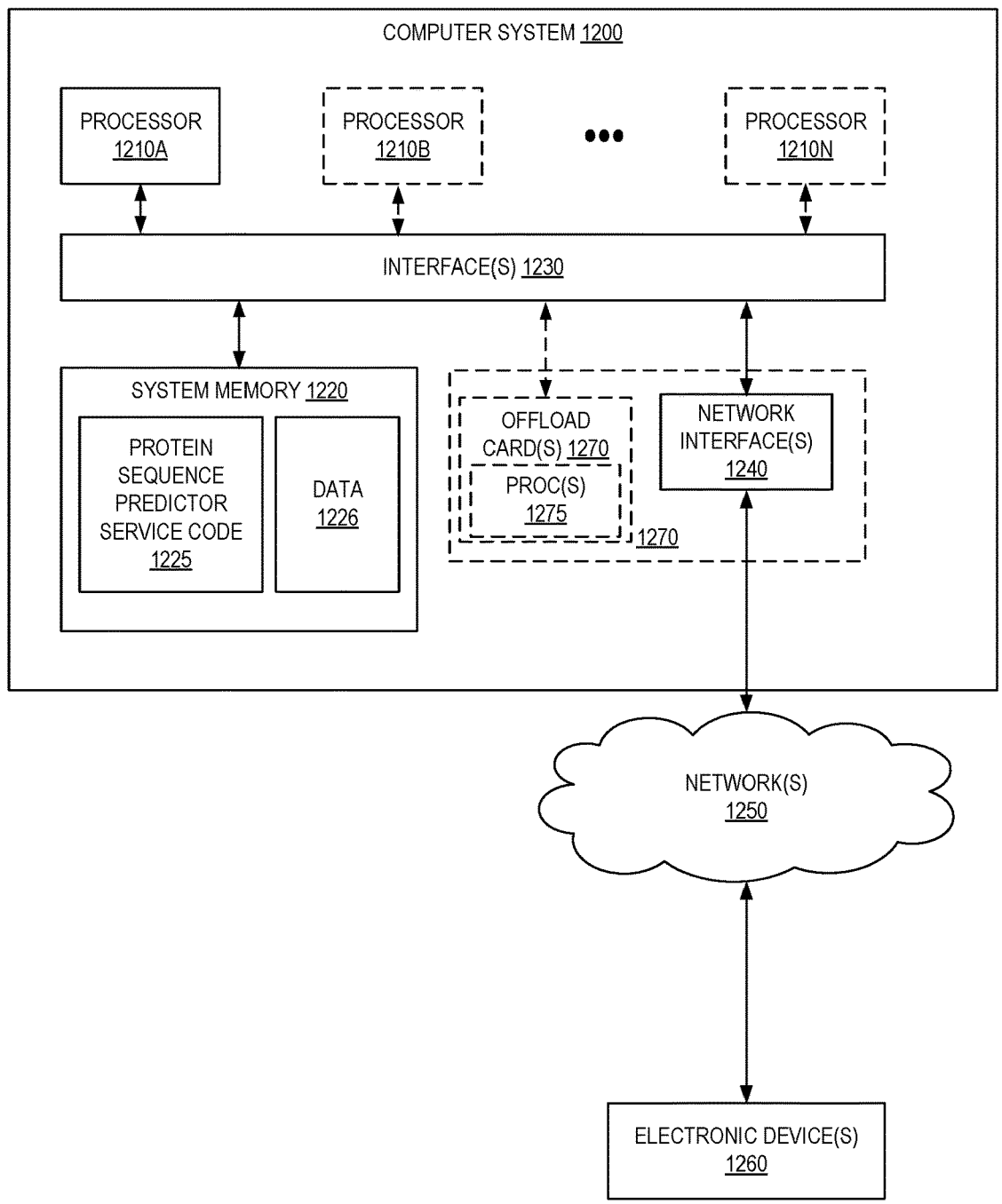
FIG. 12 is a block diagram illustrating an example computer system that may be used in some embodiments.

In some embodiments, a system that implements a portion or all of the techniques described herein may include a general-purpose computer system that includes or is configured to access one or more computer-accessible media, such as computer system 1200 illustrated in FIG. 12. In the illustrated embodiment, computer system 1200 includes one or more processors 1210 coupled to a system memory 1220 via an input/output (I/O) interface 1230. Computer system 1200 further includes a network interface 1240 coupled to I/O interface 1230. While FIG. 12 shows computer system 1200 as a single computing device, in various embodiments a computer system 1200 may include one computing device or any number of computing devices configured to work together as a single computer system 1200.

In various embodiments, computer system 1200 may be a uniprocessor system including one processor 1210, or a multiprocessor system including several processors 1210 (e.g., two, four, eight, or another suitable number). Processors 1210 may be any suitable processors capable of executing instructions. For example, in various embodiments, processors 1210 may be general-purpose or embedded processors implementing any of a variety of instruction set architectures (ISAs), such as the x86, ARM, PowerPC, SPARC, or MIPS ISAs, or any other suitable ISA. In multiprocessor systems, each of processors 1210 may commonly, but not necessarily, implement the same ISA.

System memory 1220 may store instructions and data accessible by processor(s) 1210. In various embodiments, system memory 1220 may be implemented using any suitable memory technology, such as random-access memory (RAM), static RAM (SRAM), synchronous dynamic RAM (SDRAM), nonvolatile/Flash-type memory, or any other type of memory. In the illustrated embodiment, program instructions and data implementing one or more desired functions, such as those methods, techniques, and data described above are shown stored within system memory 1220 as protein predictor service code 1225 and data 1226.

In one embodiment, I/O interface 1230 may be configured to coordinate I/O traffic between processor 1210, system memory 1220, and any peripheral devices in the device, including network interface 1240 or other peripheral interfaces. In some embodiments, I/O interface 1230 may perform any necessary protocol, timing or other data transformations to convert data signals from one component (e.g., system memory 1220) into a format suitable for use by another component (e.g., processor 1210). In some embodiments, I/O interface 1230 may include support for devices attached through various types of peripheral buses, such as a variant of the Peripheral Component Interconnect (PCI) bus standard or the Universal Serial Bus (USB) standard, for example. In some embodiments, the function of I/O interface 1230 may be split into two or more separate components, such as a north bridge and a south bridge, for example. Also, in some embodiments some or all of the functionality of I/O interface 1230, such as an interface to system memory 1220, may be incorporated directly into processor 1210.

Network interface 1240 may be configured to allow data to be exchanged between computer system 1200 and other devices 1260 attached to a network or networks 1250, such as other computer systems or devices as illustrated in FIG. 1, for example. In various embodiments, network interface 1240 may support communication via any suitable wired or wireless general data networks, such as types of Ethernet network, for example. Additionally, network interface 1240 may support communication via telecommunications/telephony networks such as analog voice networks or digital fiber communications networks, via storage area networks (SANs) such as Fibre Channel SANs, or via I/O any other suitable type of network and/or protocol.

In some embodiments, a computer system 1200 includes one or more offload cards 1270 (including one or more processors 1275, and possibly including the one or more network interfaces 1240) that are connected using an I/O interface 1230 (e.g., a bus implementing a version of the Peripheral Component Interconnect Express (PCI-E) standard, or another interconnect such as a QuickPath interconnect (QPI) or UltraPath interconnect (UPI)). For example, in some embodiments the computer system 1200 may act as a host electronic device (e.g., operating as part of a hardware virtualization service) that hosts compute instances, and the one or more offload cards 1270 execute a virtualization manager that can manage compute instances that execute on the host electronic device. As an example, in some embodiments the offload card(s) 1270 can perform compute instance management operations such as pausing and/or un-pausing compute instances, launching and/or terminating compute instances, performing memory transfer/copying operations, etc. These management operations may, in some embodiments, be performed by the offload card(s) 1270 in coordination with a hypervisor (e.g., upon a request from a hypervisor) that is executed by the other processors 1210A-1210N of the computer system 1200. However, in some embodiments the virtualization manager implemented by the offload card(s) 1270 can accommodate requests from other entities (e.g., from compute instances themselves), and may not coordinate with (or service) any separate hypervisor.

In some embodiments, system memory 1220 may be one embodiment of a computer-accessible medium configured to store program instructions and data as described above. However, in other embodiments, program instructions and/or data may be received, sent, or stored upon different types of computer-accessible media. Generally speaking, a computer-accessible medium may include non-transitory storage media or memory media such as magnetic or optical media, e.g., disk or DVD/CD coupled to computer system 1200 via I/O interface 1230. A non-transitory computer-accessible storage medium may also include any volatile or non-volatile media such as RAM (e.g., SDRAM, double data rate (DDR) SDRAM, SRAM, etc.), read only memory (ROM), etc., that may be included in some embodiments of computer system 1200 as system memory 1220 or another type of memory. Further, a computer-accessible medium may include transmission media or signals such as electrical, electromagnetic, or digital signals, conveyed via a communication medium such as a network and/or a wireless link, such as may be implemented via network interface 1240.

Various embodiments discussed or suggested herein can be implemented in a wide variety of operating environments, which in some cases can include one or more user computers, computing devices, or processing devices which can be used to operate any of a number of applications. User or client devices can include any of a number of general-purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially available operating systems and other known applications for purposes such as development and database management. These devices also can include other electronic devices, such as dummy terminals, thin-clients, gaming systems, and/or other devices capable of communicating via a network.

Most embodiments utilize at least one network that would be familiar to those skilled in the art for supporting communications using any of a variety of widely-available protocols, such as Transmission Control Protocol/Internet Protocol (TCP/IP), File Transfer Protocol (FTP), Universal Plug and Play (UPnP), Network File System (NFS), Common Internet File System (CIFS), Extensible Messaging and Presence Protocol (XMPP), AppleTalk, etc. The network(s) can include, for example, a local area network (LAN), a wide-area network (WAN), a virtual private network (VPN), the Internet, an intranet, an extranet, a public switched telephone network (PSTN), an infrared network, a wireless network, and any combination thereof.

In embodiments utilizing a web server, the web server can run any of a variety of server or mid-tier applications, including HTTP servers, File Transfer Protocol (FTP) servers, Common Gateway Interface (CGI) servers, data servers, Java servers, business application servers, etc. The server(s) also may be capable of executing programs or scripts in response requests from user devices, such as by executing one or more Web applications that may be implemented as one or more scripts or programs written in any programming language, such as Java®, C, C # or C++, or any scripting language, such as Perl, Python, PHP, or TCL, as well as combinations thereof. The server(s) may also include database servers, including without limitation those commercially available from Oracle®, Microsoft®, Sybase®, IBM®, etc. The database servers may be relational or non-relational (e.g., "NoSQL"), distributed or non-distributed, etc.

Environments disclosed herein can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and/or at least one output device (e.g., a display device, printer, or speaker). Such a system may also include one or more storage devices, such as disk drives, optical storage devices, and solid-state storage devices such as random-access memory (RAM) or read-only memory (ROM), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, Electrically Erasable Programmable Read-Only Memory (EEPROM), flash memory or other memory technology, Compact Disc-Read Only Memory (CD-ROM), Digital Versatile Disk (DVD) or other optical storage, magnetic cassettes, magnetic tape, magnetic disk storage or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

In the preceding description, various embodiments are described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Bracketed text and blocks with dashed borders (e.g., large dashes, small dashes, dot-dash, and dots) are used herein to illustrate optional operations that add additional features to some embodiments. However, such notation should not be taken to mean that these are the only options or optional operations, and/or that blocks with solid borders are not optional in certain embodiments.

Reference numerals with suffix letters may be used to indicate that there can be one or multiple instances of the referenced entity in various embodiments, and when there are multiple instances, each does not need to be identical but may instead share some general traits or act in common ways. Further, the particular suffixes used are not meant to imply that a particular amount of the entity exists unless specifically indicated to the contrary. Thus, two entities using the same or different suffix letters may or may not have the same number of instances in various embodiments.

References to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Moreover, in the various embodiments described above, unless specifically noted otherwise, disjunctive language such as the phrase "at least one of A, B, or C" is intended to be understood to mean either A, B, or C, or any combination thereof (e.g., A, B, and/or C). As such, disjunctive language is not intended to, nor should it be understood to, imply that a given embodiment requires at least one of A, at least one of B, or at least one of C to each be present.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

What is claimed is:

1. A computer-implemented method comprising:
   receiving, at a protein sequence predictor comprising one or more processors, a request to predict a missing area of a protein primary sequence and a corresponding three-dimensional position of the missing area, the request including a representation of the protein primary sequence, backbone Cartesian coordinates for the protein primary sequence, and an indication of ablations in the protein primary sequence;
   conditioning the protein primary sequence and the backbone Cartesian coordinates for the protein primary sequence by:
      passing the representation of the protein primary sequence as input to an attention-based machine learning model of the protein sequence predictor and applying an embedding of the attention-based machine learning model to the representation of the protein primary sequence,
      obtaining output of a protein vector from the attention-based machine learning model,
      passing the backbone Cartesian coordinates as input to the protein sequence predictor to capture features in sequence space, and
      obtaining output of processed backbone Cartesian coordinates from the protein sequence predictor;
   combining the processed backbone Cartesian coordinates and the protein vector to generate a combined coordinate vector and protein vector;
   passing the combined coordinate vector and protein vector as input to the attention-based machine learning model;
   obtaining output of a prediction of the missing area of the protein primary sequence and the corresponding three-dimensional position of the missing area from the attention-based machine learning model;
   and
   generating a three-dimensional representation of the protein based on the output of the prediction of the missing area of the protein primary sequence and the corresponding three-dimensional position of the missing area.

2. The computer-implemented method of claim 1, wherein the representation of the protein primary sequence uses an amino acid code consistent with International Union of Pure and Applied Chemistry usage.

3. The computer-implemented method of claim 1, wherein the attention-based machine learning model is a transformer-based model.

4. A computer-implemented method comprising:
   receiving, at a protein sequence predictor comprising one or more processors, a request to predict a missing area of a protein primary sequence and a corresponding three-dimensional position of the missing area;

passing as input to a machine learning model of the protein sequence predictor backbone Cartesian coordinates of the protein primary sequence and a protein vector of a representation of the protein primary sequence including the missing area, wherein the machine learning model is selected from the group consisting of: an attention-based machine learning model, a bidirectional long short term memory-based model, and a convolutional neural network-based model; and obtaining output of a prediction of the missing area of the protein primary sequence and the corresponding three-dimensional position of the missing area from the machine learning model.

5. The computer-implemented method of claim 4, further comprising:

applying an embedding of the machine learning model to the representation of the protein primary sequence to generate the protein vector.

6. The computer-implemented method of claim 5, wherein the representation of the protein primary sequence is a character-based representation.

7. The computer-implemented method of claim 6, wherein characters of the character-based representation conform to an amino acid code consistent with International Union of Pure and Applied Chemistry usage.

8. The computer-implemented method of claim 6, wherein the request includes an indication of regions of ablation using a set of mask tokens in the representation of the protein primary sequence.

9. The computer-implemented method of claim 4, wherein the request includes processed backbone Cartesian coordinates for the protein primary sequence and an embedded representation of the protein primary sequence as the protein vector.

10. The computer-implemented method of claim 4, wherein the machine learning model is a transformer-based model.

11. The computer-implemented method of claim 4, wherein the machine learning model is a convolutional neural network-based model comprising a stack of residual block layers.

12. The computer-implemented method of claim 4, wherein the machine learning model is a long short term memory-based model comprising a stack of bidirectional long short term memory-based layers.

13. The computer-implemented method of claim 4, further comprising:

generating a 3-D representation from the output of the machine learning model.

14. The computer-implemented method of claim 4, further comprising:

combining the backbone Cartesian coordinates of the protein primary sequence and the protein vector of the representation of the protein primary sequence prior to passing the input to the machine learning model.

15. A system comprising:

a first one or more electronic devices to implement a three-dimensional generation service in a multi-tenant provider network; and a second one or more electronic devices to implement a protein sequence predictor service in the multi-tenant provider network, the protein sequence predictor service including memory storing instructions that upon execution by one or more processors of the protein sequence predictor service, cause the protein sequence predictor service to:

receive a request to predict a missing area of a protein primary sequence and a corresponding three-dimensional position of the missing area, pass as input to a machine learning model of the protein sequence predictor service backbone Cartesian coordinates of the protein primary sequence and a protein vector of a representation of the protein primary sequence including the missing area, wherein the machine learning model is selected from the group consisting of: an attention-based machine learning model, a bidirectional long short term memory-based model, and a convolutional neural network-based model, and obtain output of a prediction of the missing area of the protein primary sequence and the corresponding three-dimensional position of the missing area from the machine learning model, wherein the three-dimensional generation service is to generate a three-dimensional representation of the output.

16. The system of claim 15, wherein the protein sequence predictor service is to apply an embedding of the machine learning model to the representation of the protein primary sequence to generate the protein vector.

17. The system of claim 16, wherein the representation of the protein primary sequence is a character-based representation.

18. The system of claim 17, wherein characters of the character-based representation conform to an amino acid code consistent with International Union of Pure and Applied Chemistry usage.

19. The system of claim 15, wherein the request includes an indication of regions of ablation using a set of mask tokens in the representation of the protein primary sequence.

20. The system of claim 15, wherein the request includes processed backbone Cartesian coordinates for the protein primary sequence and an embedded representation of the protein primary sequence as the protein vector.

\* \* \* \* \*